United States Patent [19]

Wada et al.

[11] Patent Number: 4,716,110
[45] Date of Patent: Dec. 29, 1987

[54] COMPOSITION FOR ASSAYING HYDROGEN PEROXIDE

[75] Inventors: Hiroshi Wada, Chigasaki; Yuzo Kosaka, Adachi, both of Japan

[73] Assignee: Eiken Kagaku Kabushiki Kaisha, Japan

[21] Appl. No.: 664,309

[22] Filed: Oct. 24, 1984

[30] Foreign Application Priority Data

Aug. 22, 1984 [JP] Japan .................. 59-174630

[51] Int. Cl.[4] .................. C12Q 1/26; C12Q 1/28; C12Q 1/54
[52] U.S. Cl. .................. 435/25; 435/28; 435/14; 435/805
[58] Field of Search .................. 435/14, 25, 28, 805

[56] References Cited

U.S. PATENT DOCUMENTS

| | | | |
|---|---|---|---|
| 3,123,443 | 3/1964 | Smeby | 23/253 |
| 4,008,267 | 2/1977 | Jönsson et al. | 435/14 |
| 4,211,845 | 7/1980 | Genshaw et al. | 435/14 |
| 4,273,868 | 6/1981 | Walter | 435/14 |
| 4,318,985 | 3/1982 | Bauer et al. | 435/14 |
| 4,353,984 | 10/1982 | Yamada et al. | 435/14 |
| 4,361,648 | 11/1982 | Shuenn-tzong | 435/10 |
| 4,385,114 | 5/1983 | Guthlein et al. | 435/28 |
| 4,396,714 | 8/1983 | Maeda et al. | 435/14 |
| 4,503,143 | 3/1985 | Gerber et al. | 435/28 |

*Primary Examiner*—Esther M. Kepplinger
*Attorney, Agent, or Firm*—Parkhurst & Oliff

[57] ABSTRACT

The present invention provides a composition for assaying hydrogen peroxide having an enzyme, a buffer and a chromogen, wherein the chromogen is a sulfoalkyl derivative of a 3,3',5,5'-tetraalkylbenzidine or a water-soluble salt thereof represented by the following general formula I:

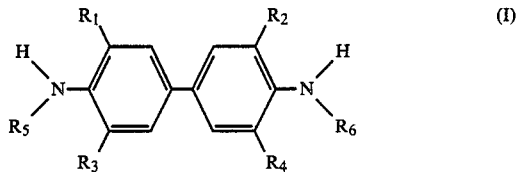

(I)

wherein $R_1$, $R_2$, $R_3$ and $R_4$ may be the same or different and each represent a straight-chain alkyl group having 1 to 6 carbon atoms, such as a methyl, ethyl, n-propyl, n-butyl, n-amyl or n-hexyl group. $R_5$ and $R_6$ each represent a hydrogen atom or a sulfoalkyl group of the following formula II:

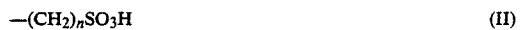

$$-(CH_2)_n SO_3 H \qquad (II)$$

wherein n represents an integer of 1 to 6, with the proviso that either $R_5$ and $R_6$ represents a sulfoalkyl group and the sulfoalkyl group may be substituted with at least 1, preferably 1 to 2 hydroxyl groups. This composition has a high solubility in water and is usable over a wide pH range and for the preparation of both a test solution and a test piece. Various modifications of the composition are possible. Therefore, by using the composition, components of a body fluid can be assayed quantitatively in a precise, easy and rapid manner.

18 Claims, 3 Drawing Figures

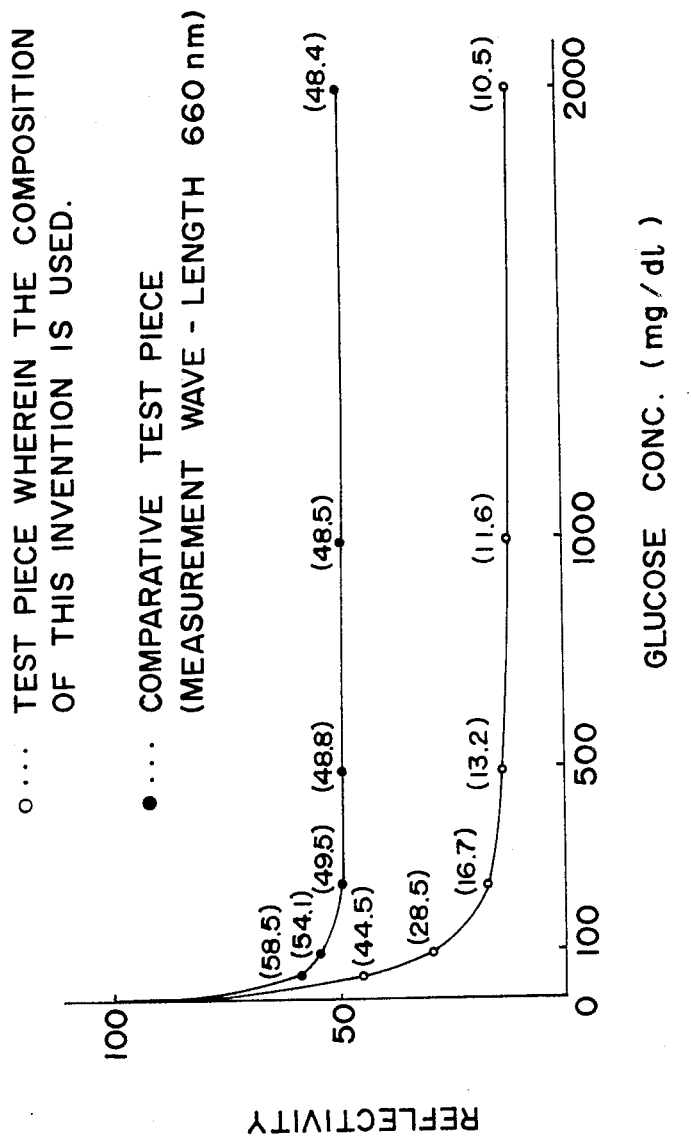

COMPOSITION FOR ASSAYING HYDROGEN PEROXIDE

BACKGROUND OF THE INVENTION

1. Field of the Invention

The present invention relates to a reagent composition used for assaying hydrogen peroxide contained in a liquid, particularly, a body fluid.

2. Description of the Prior Art

Currently, hydrogen peroxide assay is very extensively used in clinical examinations in the medical field and in various other fields such as the chemical industry, food industry and public sanitation industry. Particularly in the clinical examinations are, the methods for analyzing body fluids with enzymes have spread rapidly. Among these methods, the hydrogen peroxide assay is very important, since numerous components of the body fluid can be assayed by a relatively simple method wherein the body fluid is reacted with an oxidase to form hydrogen peroxide and the resulting hydrogen peroxide is measured. Typical combinations of a component/oxidase include, for example, glucose/glucose oxidase, cholesterol/cholesterol oxidase, uric acid/uricase, amino acid/amino acid oxidase and pyruvic acid/pyruvic acid oxidase.

The hydrogen peroxide thus formed may be assayed by various methods. The most generally employed method comprises oxidizing a chromogen in the presence of a peroxidase to form a pigment and determining the latter colorimetrically. The chromogen thus selected generally has amino and hydroxyl groups in the molecule, a high stability and a high pigment-forming power. The most frequently used chromogen is a combination of 4-aminoantipyrine and phenol known as "Trinder reagent". Recently, numerous modifications of this chromogen have been reported.

In the field of so-called "dry chemistry" in which a reagent composition used for the assay of a body fluid composition is fixed on a carrier, a benzidine derivative, particularly o-tolidine has been preferably used as the chromogen. This is because the use of this substance as the chromogen is advantageous in that a quite sharp sensitivity is obtained and a pigment which has a maximum absorption on the long wave-length side in the visible light region is formed with the result that it is not easily influenced by various coloring components present therein. However, o-tolidine is thought to be carcinogenic so that a special care must be taken in the production of testing implements containing this compound.

Recently, a chromogen having the characteristic properties of o-tolidine but free of carcinogenicity has been developed. This is a benzidine compound having methyl groups in positions 3, 3', 5 and 5' [see V. R. Holland et al., "Tetrahedron", 30, 3299 to 3302 (1974)]. Further, it is disclosed in the specification of West German Pat. No. 2,460,903 that benzidine substituted with alkyl groups other than methyl group in positions 3, 3', 5 and 5' is also usable as the chromogen.

However, these benzidine derivatives have a quite poor solubility in water and, therefore, they can be used in only a limited concentration range in an acidic pH region. This is a serious defect, since the enzymatic assay of body fluids is effected in a neutral region in most cases. It is because of this defect that the benzidine derivatives have been used mainly for the preparation of test pieces only. However, even the test pieces containing the benzidine derivatives cannot completely overcome the disadvantages due to the above-mentioned defect so that they are usable only when the amount of hydrogen peroxide formed is very small.

Attempts have been made for broadening the concentration range of hydrogen peroxide to be assayed, one of which is a process wherein the benzidine derivatives are used in admixture with another chromogen (see the specification of Japanese Patent Publication No. 5520/1982).

The poor solubility of 3,3',5,5'-tetraalkylbenzidine in water causes another disadvantage in the preparation of the test pieces. For example, when 3,3',5,5'-tetraalkylbenzidine is selected as the chromogen in the preparation of an aqueous impregnation solution generally comprising an enzyme, a buffer and a chromogen in the course of the preparation of the test pieces for assaying glucose in a body fluid, it is quite difficult to obtain a homogeneous, aqueous impregnation solution. Processes which have been proposed to overcome this defect include one which comprises two steps of impregnation of the enzyme and the buffer and impregnation of the chromogen (see the specification of Japanese Patent Publication No. 29160/1982) and one wherein a mordant is added to the aqueous chromogen impregnation solution (see the specification of U.S. Pat. No. 4,361,648).

After intensive investigations made with due regard to the above-mentioned defects, the inventors have completed the present invention.

SUMMARY OF THE INVENTION

An object of the present invention is to solve the problems of the prior techniques. Namely, the object is to provide a composition for assaying hydrogen peroxide which retains the characteristic properties of 3,3',5,5'-tetraalkylbenzidine, has a high solubility in water and is usable in a wide pH region and for the production of both a test solution and a test piece.

The present invention provides a composition for assaying hydrogen peroxide comprising an enzyme, a buffer and a chromogen, characterized by containing as the chromogen a sulfoalkyl derivative of a 3,3',5,5'-tetraalkylbenzidine or a water-soluble salt thereof represented by the following general formula I:

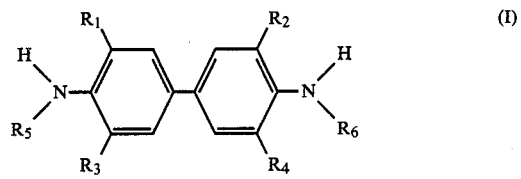

wherein $R_1$, $R_2$, $R_3$ and $R_4$ may be the same or different and each represent a straight-chain alkyl group having 1 to 6 carbon atoms, such as a methyl, ethyl, n-propyl, n-butyl, n-amyl or n-hexyl group, and $R_5$ and $R_6$ each represent a hydrogen atom or a sulfoalkyl group of the following formula II:

in which n represents an integer of 1 to 6, with the proviso that either $R_5$ or $R_6$ represents a sulfoalkyl group and the sulfoalkyl group may be substituted with at least 1, preferably 1 to 2 hydroxyl groups.

BRIEF DESCRIPTION OF THE DRAWINGS

FIG. 3 is a graph showing a relationship between the glucose concentration determined by using the test piece containing the composition of the present invention and a comparative test piece and a reflectivity at a given wave-length on the surface of the test paper read from a color-difference meter.

DETAILED DESCRIPTION OF THE INVENTION

Figure 1:
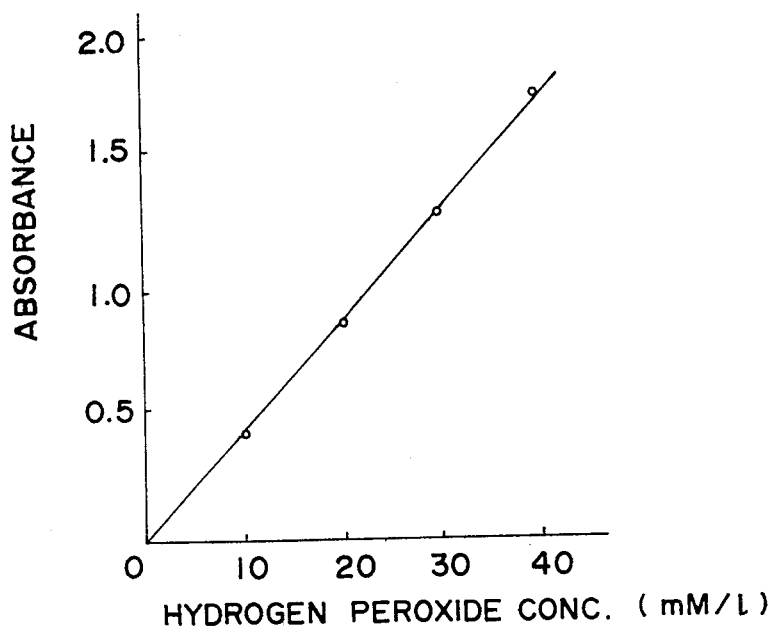
FIG. 1 is a graph showing a calibration curve prepared by using the composition for assaying hydrogen peroxide of the present invention.

The inventors have found that when the compound of the above general formula (I) or the water-soluble salt thereof is used as the chromogen, hydrogen peroxide of even a high concentration can be assayed quantitatively in a highly sensitive manner.

The compounds preferably used in the present invention include, for example, the following compounds, though not limited thereto:

N-(2-sulfoethyl)-3,3',5,5'-tetramethylbenzidine,
N-(3-sulfopropyl)-3,3',5,5'-tetramethylbenzidine,
N-(4-sulfobutyl)-3,3',5,5'-tetramethylbenzidine,
N-(3-sulfopropyl)-3,3',5,5'-tetraethylbenzidine,
N-(2-hydroxy-3-sulfopropyl)-3,3',5,5'-tetramethylbenzidine,
N,N'-bis(2-sulfoethyl)-3,3',5,5'-tetramethylbenzidine,
N,N'-bis(3-sulfopropyl)-3,3',5,5'-tetramethylbenzidine,
N,N'-bis(4-sulfobutyl)-3,3',5,5'-tetramethylbenzidine,
N,N'-bis(3-sulfopropyl)-3,3',5,5'-tetraethylbenzidine,
N,N'-bis(2-hydroxy-2-sulfoethyl)-3,3',5,5'-tetramethylbenzidine, and
N,N'-bis(2-hydroxy-3-sulfopropyl)-3,3',5,5'-tetramethylbenzidine.

These compounds may be used alone or in the form of a combination of two or more of them as the chromogen. Further, these compounds may be combined also with other chromogens.

Though most of these compounds have not been disclosed in literature as yet, they can be prepared easily by known processes.

For example, these compounds can be obtained by reacting a 3,3',5,5'-tetraalkylbenzidine with a corresponding sultone [see Oda et al. "Kogyo Kagaku Zasshi" 59, No. 9, 1028 to 1030 (1956)] or by reacting a 3,3',5,5'-tetraalkylbenzidine with an alkylsulfonic acid or hydroxylalkylsulfonic acid having a halogen at a molecular end [see N. E. Good et al., "Analytical Biochemistry", 104, 300 to 310 (1980)].

The 3,3',5,5'-tetraalkylbenzidine derivatives contained in the composition of the present invention may be used in place of any chromogen which has been used heretofore for assaying hydrogen peroxide. These derivatives are particularly advantageously used for an enzymatic assay of a body fluid composition in which hydrogen peroxide is formed in the course of the analysis. This is because the compounds of the present invention have the following many advantages: the compounds having a high solubility particularly in water can be mixed with a buffer and an enzyme to form a stable, homogeneous test solution. By using these compounds, hydrogen peroxide of even a high concentration can be assayed with a high sensitivity. The compounds are not easily influenced by other coloring components contained therein.

When the chromogen compound used for the production of the composition of the present invention is incorporated in an absorptive carrier together with the enzyme and the buffer and the carrier is applied to a support made of, for example, plastic so as to use it conveniently, a test implement having an excellent storage stability and being usable easily is obtained. The most frequently used absorptive carrier is filter paper. In addition, nonwoven fabrics, cotton and wood chips may also be used. It is also possible to apply the testing reagent composition to a support such as a plastic sheet together with a suitable adhesive such as gelatin or a synthetic resin. After drying, the composition is fixed on the support. It will be understood that various modifications can be readily obtained.

DESCRIPTION OF THE PREFERRED EMBODIMENTS

The following examples will further illustrate the present invention, which by no means limit the invention.

Preparation of chromogen compounds:

Preparation Example 1

Synthesis of sodium salt of N-(3-sulfopropyl)-3,3',5,5'-tetramethylbenzidine:

24.0 g of 3,3',5,5'-tetramethylbenzidine was dissolved in 100 ml of 1-propanol. 24.4 g of 1,3-propanesultone was dissolved in 100 ml of methanol and the resulting solution was added to the above-mentioned solution. The obtained mixture was heated under reflux for about 3 h. After cooling to room temperature followed by neutralization with a 1N aqueous NaOH solution, the solvent was evaporated to dryness. After recrystallization using a mixed solvent of methanol and acetone, 20 g of white crystals was obtained (yield: 53%).

Thin layer chromatography [silica gel plate (a product of Merck Co.); developer: 2-propanol/acetic acid/water=50/15/20], UV absorption observed, ninhydrin reaction (+), Rf=0.25, Infrared absorption spectrum:
$\nu$NH 3400 cm$^{-1}$,
$\nu$C=C 1620 cm$^{-1}$, $\nu$CN 1260 cm$^{-1}$,
$\nu$SO$_3$ 1200, 1050 cm$^{-1}$

Preparation Example 2

Synthesis of sodium salt of N,N'-bis(2-hydroxy-2-sulfoethyl)-3,3',5,5'-tetramethylbenzidine:

12.02 g of 3,3',5,5'-tetramethylbenzidine was dissolved in 500 ml of 2-propanol. 52 g of sodium 2chloro-1-hydroxyethanesulfonate was dissolved in 300 ml of water and the resulting solution was added to the above-mentioned solution. 4 g of NaOH was added thereto and the mixture was heated under reflux for about 16 h. After cooling to room temperature, the solvent was evaporated to dryness. The residue was dissolved in methanol and subjected to chromatography using a silica gel-filled column (Silica Gel No. 1 for column chromatography; a product of Nakarai Kagaku Co.) to effect gradient elution (solvent: chloroform/methanol). The respective eluates were subjected to thin layer chromatography [silica gel plate (a product of Merck Co.); developer: 2-propanol/acetic acid/water=50/15/20]. A fraction having a UV absorption at Rf of 0.07 was collected. The solvent was removed to obtain 5.3 g (yield: 20%) of white crystals.

Infrared absorption spectrum:
νOH 3500 cm$^{-1}$, νNH 3400 cm$^{-1}$,
νC=C 1620 cm$^{-1}$, νCN 1260 cm$^{-1}$,
νSO$_3$ 1200, 1050 cm$^{-1}$ Preparation of the composition for assaying hydrogen peroxide:

Example 1

200 mg of sodium salt of N,N'-bis(3-sulfopropyl)-3,3',5,5'-tetramethylbenzidine, 10 mg of a peroxidase (100 IU/mg), 1.21 g of tris(hydroxymethyl)aminomethane, 210 g of citric acid (monohydrate) and 0.85 g of sodium hydroxide were dissolved in purified water to prepare 100 ml of a reactant solution (pH of 6.5).

Example 2

0.96 g of glucose oxidase (1200 (IU/g), 0.15 g of a peroxidase (100 IU/mg), 5.0 g of polyvinylyrrolidone (MW: 40,000), 0.8 g of sodium salt of N-(3-sulfopropyl)-3,3',5,5'-tetramethylbenzidine, 1.98 g of citric acid (monohydrate), 10.44 g of trisodium citrate (dihydrate) and 0.1 g of EDTA.2Na were dissolved in purified water to obtain 100 ml of a reactant solution.

Preparation of a calibration curve for hydrogen peroxide assay:

3.0 ml of the reactant solution containing the composition of the present invention prepared in Example 1 was added to 10 μl of each of 0, 10, 20, 30 and 40 mM/l aqueous hydrogen peroxide solutions. The immersion was effected in a constant temperature bath at 37° C. for 5 min to develop a color. After cooling to 25° C., the absorbance (or the optical density, O.D.) was measured at a wave-length of 665 nm. By deducting an absorbance of a blank from the absorbance measured above, ΔO.D. was determined. A calibration curve was prepared by plotting the hydrogen peroxide concentration as abscissae and ΔO.D. values as ordinates. As shown in FIG. 1, the calibration curve was a straight line drawn through the origin up to a hydrogen peroxide concentration of 40 mM/l. It will be understood, therefore, that the hydrogen peroxide concentration could be determined precisely by the colorimetric analysis.

Preparation of test pieces for assaying glucose in urine:

A filter paper (No. 2316; a product of Schleicher and Schull) was immersed in the reactant solution prepared in Example 2 and then dried at 60° C. for 30 min. The resulting test paper was cut into a piece of 5 mm×5 mm and applied to a polystyrene sheet of 5 mm×60 mm with an adhesive tape to obtain a test piece for assaying glucose in urine.

Figure 2:
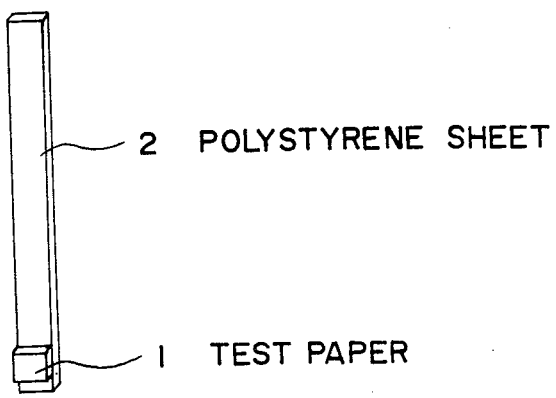
FIG. 2 is a perspective view of an embodiment of a test piece for assaying glucose in urine prepared by using the composition of the present invention.

The test piece is shown in FIG. 2, wherein 1 indicates the test piece and 2 indicates a polystyrene sheet.

Preparation of comparative test pieces:

The same filter paper as above was immersed in the same impregnation solution of the composition of the present invention except that sodium salt of N-(3-sulfopropyl)-3,3'5,5'-tetramethylbenzidine was omitted. After drying at 60° C. for 30 min, the paper was again immersed in a 0.5% solution of 3,3',5,5'-tetramethylbenzidine in acetone and then dried under vacuum. The resulting test paper was treated in the same manner as above to obtain a comparative test piece.

Determination of glucose concentration:

The test pieces prepared by using the composition of the present invention and the comparative test pieces were immersed for a moment in standard glucose solutions of various concentrations. After removing a superfluous solution, the reaction was carried out for exactly 20 sec. The reflectivity of the test pieces at a wavelength of 660 nm was determined with a color difference meter (Color Difference Computer ND-504 DE; a product of Nihon Denshoku Co.). A calibration curve shown in FIG. 3 was obtained by plotting the glucose concentrations as abscissae and the reflectivities as ordinates.

It will be understood from FIG. 3 that as compared with the test piece according to the present invention, the test piece (comparative) prepared by using tetramethylbenzidine as the chromogen had a lower sensitivity in a low glucose concentration region and a lower reflectivity change when the glucose concentration was higher than 50 mg/dl. The test piece had a substantially constant reflectivity when the glucose concentration was higher than 250 mg/dl. Therefore, the glucose concentration range measurable with the test piece was 0 to 250 mg/dl.

On the other hand, the test piece according to the present invention had a higher sensitivity than the comparative one. A clear reflectivity change could be recognized when the glucose concentration was as high as 2000 mg/dl. Therefore, the glucose concentration range measurable with this test piece was 0 to 2,000 mg/dl. Thus, it is evident that as compared with the comparative test piece prepared by using the conventional composition for assaying hydrogen peroxide, the test piece prepared by using the composition for assaying hydrogen peroxide according to the present invention was usable over a wider glucose concentration range. As a matter of course, when a suitable enzyme and a suitable buffer are contained in addition to glucose in the composition of the present invention, the composition and the test piece prepared by using it can be used for assaying various components of a body fluid.

As described above, as compared with the conventional composition for assaying hydrogen peroxide containing the 3,3',5,5'-tetraalkylbenzidine as the chromogen, the composition of the present invention for assaying hydrogen peroxide containing the sulfoalkyl derivative of the 3,3',5,5'-tetraalkylbenzidine or the water-soluble salt thereof as the chromogen has a remarkably improved solubility in water so that it is usable over a wider pH range.

Further, by virtue of the improved water solubility, it becomes possible to effect the quantitative determination of components in an aqueous solution with a higher sensitivity and over a wider concentration range.

In addition, since the composition for assaying hydrogen peroxide in the form of an aqueous solution thereof can be supported on a carrier in only one step in the preparation of the test pieces for assaying the components of the body fluid, the process for the preparation of the test pieces can be simplified. The resulting test pieces are usable over a wider concentration range with a higher sensitivity than those of the test pieces prepared from the conventional composition.

Thus, the composition of the present invention for assaying hydrogen peroxide may be used in the form of either a test piece or an aqueous solution thereof and various modifications thereof are possible. The composition exhibits, therefore, excellent effects in the precise, easy and rapid quantitative assay of components of body fluids.

What is claimed is:

1. A composition for assaying hydrogen peroxide comprising an enzyme, a buffer and a chromogen, wherein said chromogen comprises a sulfoalkyl derivative of a 3,3',5,5'-tetraalkylbenzidine or a water-soluble salt thereof represented by the following general formula I:

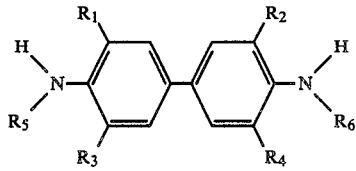

wherein $R_1$, $R_2$, $R_3$ and $R_4$ are straight-chain alkyl groups having 1 to 6 carbon atoms, selected from the group consisting of a methyl, ethyl, n-propyl, n-butyl, n-amyl and n-hexyl group, and one of $R_5$ and $R_6$ represents a sulfoalkyl group of the following formula II:

$$-(CH_2)_n SO_3 H \qquad (II)$$

wherein n represents an integer of 1 to 6 and wherein the sulfoalkyl group is substituted with at least one hydroxyl group, the other one of $R_5$ and $R_6$ representing a member selected from the the group consisting of a hydrogen atom and said sulfoalkyl group.

2. A composition for assaying hydrogen peroxide according to claim 1, wherein said chromogen of the general formula I is N,N'-bis(2-hydroxy-2-sulfoethyl)-3,3',5,5'-tetramethylbenzidine.

3. A composition for assaying hydrogen peroxide according to claim 1, wherein said enzyme is selected from the group consisting of glucose oxidase and peroxidase.

4. A composition for assaying hydrogen peroxide according to claim 1, wherein said enzyme, said buffer and said chromogen of the general formula I or water-soluble salt thereof are dissolved in water.

5. A composition for assaying hydrogen peroxide according to claim 1, wherein said chromogen of the general formula I is a compound selected from the group consisting of N-(2-hydroxy-3-sulfopropyl)-3,3',5,5'-tetramethylbenzidine, N,N'-bis(2-hydroxy-2-sulfoethyl)-3,3',5,5'-tetramethylbenzidine, and N,N'-bis(2-hydroxy-3-sulfopropyl)-3,3',5,5'-tetramethylbenzidine.

6. A test strip for assaying hydrogen peroxide comprising a composition for assaying hydrogen peroxide supported on an absorptive carrier applied to a support, wherein said composition comprises an enzyme, a buffer and a chromogen comprising a sulfoalkyl derivative of a 3,3',5,5'-tetraalkylbenzidine or a water-soluble salt thereof represented by the following general formula I:

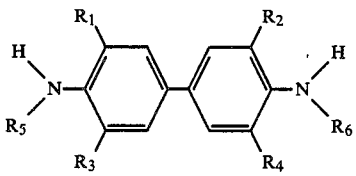

wherein $R_1$, $R_2$, $R_3$ and $R_4$ are straight-chain alkyl groups having 1 to 6 carbon atoms, selected from the group consisting of a methyl, ethyl, n-propyl, n-butyl, n-amyl and n-hexyl group, and one of $R_5$ and $R_6$ represents a sulfoalkyl group of the following formula II:

$$-(CH_2)_n SO_3 H \qquad (II)$$

wherein n represents an integer of 1 to 6 and wherein the sulfoalkyl group is substituted with at least one hydroxyl group, the other one of $R_5$ and $R_6$ representing a member selected from the group consisting of a hydrogen atom and said sulfoalkyl group.

7. A test strip for assaying hydrogen peroxide according to claim 6, wherein said chromogen of the general formula I is N,N'-bis(2-hydroxy-2-sulfoethyl)-3,3',5,5'-tetramethylbenzidine.

8. A test strip for assaying hydrogen peroxide according to claim 6, wherein said absorptive carrier is filter paper.

9. A test strip for assaying hydrogen peroxide according to claim 6, wherein said support is a plastic sheet.

10. A process for assaying hydrogen peroxide, comprising the steps of:
preparing a composition for assaying hydrogen peroxide comprising an enzyme, a buffer and a chromogen, wherein said chromogen comprises a sulfoalkyl derivative of a 3,3',5,5'-tetraalkylbenzidine or a water-soluble salt thereof represented by the following general formula I:

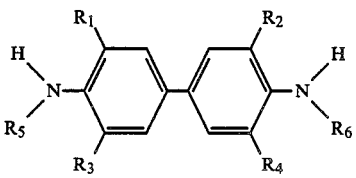

wherein $R_1$, $R_2$, $R_3$ and $R_4$ are straight-chain alkyl groups having 1 to 6 carbon atoms, selected from the group consisting of a methyl, ethyl, n-propyl, n-butyl, n-amyl and n-hexyl group, and one of $R_5$ and $R_6$ represents a sulfoalkyl group of the following formula II:

$$-(CH_2)_n SO_3 H \qquad (II)$$

wherein n represents an integer of 1 to 6 and wherein the sulfoalkyl group is substituted with at least one hydroxyl group, the other one of $R_5$ and $R_6$ representing a member selected from the group consisting of a hydrogen atom and said sulfoalkyl group; and
contacting a solution with said composition, thereby assaying the solution for hydrogen peroxide.

11. A process for assaying hydrogen peroxide comprising the steps of:
preparing a test strip for assaying hydrogen peroxide comprising a composition for assaying hydrogen peroxide supported on an absorptive carrier applied to a support, wherein said composition comprises an enzyme, a buffer and a chromogen, said chromogen comprising a sulfoalkyl derivative of a 3,3',5,5'-tetraalkylbenzidine or a water-soluble salt thereof represented by the following general formula I:

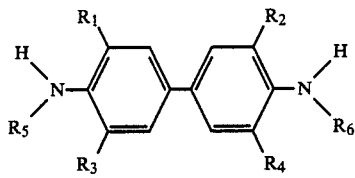

wherein $R_1$, $R_2$, $R_3$ and $R_4$ are straight-chain alkyl groups having 1 to 6 carbon atoms, selected from the group consisting of a methyl, ethyl, n-propyl, n-butyl, n-amyl and n-hexyl group, and one of $R_5$ and $R_6$ represents a sulfoalkyl group of the following formula II:

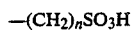

wherein n represents an integer of 1 to 6 and wherein the sulfoalkyl group is substituted with at least one hydroxyl group, the other one of $R_5$ and $R_6$ representing a member selected from the group consisting of a hydrogen atom and said sulfoalkyl group; and contacting a solution with said test strip, thereby assaying the solution for hydrogen peroxide.

12. A composition for assaying hydrogen peroxide comprising an enzyme, a buffer and a chromogen, wherein said chromogen comprises a sulfoalkyl derivative of a 3,3′,5,5′-tetraalkylbenzidine or a water-soluble salt thereof represented by the following general formula I:

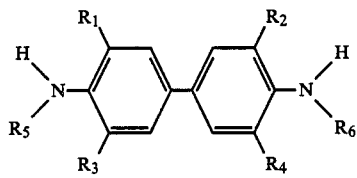

wherein $R_1$, $R_2$, $R_3$ and $R_4$ are straight-chain alkyl groups having 1 to 6 carbon atoms, selected from the group consisting of a methyl, ethyl, n-propyl, n-butyl, n-amyl and n-hexyl group, and one of $R_5$ and $R_6$ represents a sulfoalkyl group of the following formula II:

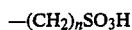

wherein n represents an integer of 1 to 6, the other one of $R_5$ and $R_6$ representing a member selected from the group consisting of a hydrogen atom and said sulfoalkyl group.

13. A composition for assaying hydrogen peroxide according to claim 12, wherein said chromogen of the general formula I is a compound selected from the group consisting of the following compounds:
N-(2-sulfoethyl)-3,3′,5,5′-tetramethylbenzidine,
N-(3-sulfopropyl)-3,3′,5,5′-tetramethylbenzidine,
N-(4-sulfobutyl)-3,3′,5,5′-tetramethylbenzidine,
N-(3-sulfopropyl)-3,3′,5,5′-tetraethylbenzidine,
N,N′-bis(2-sulfoethyl)-3,3′,5,5′-tetramethylbenzidine,
N,N′-bis(3-sulfopropyl)-3,3′,5,5′-tetramethylbenzidine,
N,N′-bis(4-sulfobutyl)-3,3′,5,5′-tetramethylbenzidine, and
N,N′-bis(3-sulfopropyl)-3,3′,5,5′-tetramethylbenzidine.

14. A composition for assaying hydrogen peroxide according to claim 12, wherein said chromogen of the general formula I is N-(3-sulfopropyl)-3,3′,5,5′-tetramethylbenzidine.

15. A test strip for assaying hydrogen peroxide comprising a composition for assaying hydrogen peroxide supported on an absorptive carrier applied to a support, wherein said composition comprises an enzyme, a buffer and a chromogen, said chromogen comprising a sulfoalkyl derivative of a 3,3′,5,5′-tetraalkylbenzidine or a water-soluble salt thereof represented by the following general formula I:

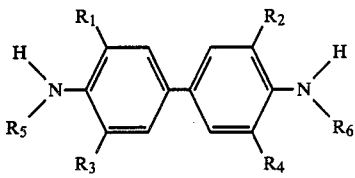

wherein $R_1$, $R_2$, $R_3$ and $R_4$ are straight-chain alkyl groups having 1 to 6 carbon atoms, selected from the group consisting of a methyl, ethyl, n-propyl, n-butyl, n-amyl and n-hexyl group, and one of $R_5$ and $R_6$ represents a sulfoalkyl group of the following formula II:

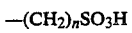

wherein n represents an integer of 1 to 6, the other one of $R_5$ and $R_6$ representing a member selected from the group consisting of a hydrogen atom and said sulfoalkyl group.

16. A test strip for assaying hydrogen peroxide according to claim 15, wherein said chromogen of the general formula I is N-(3-sulfopropyl)-3,3′,5,5′-tetramethylbenzidine.

17. A process for assaying hydrogen peroxide, comprising the steps of:
preparing a composition for assaying hydrogen peroxide comprising an enzyme, a buffer and a chromogen, wherein said chromogen comprises a sulfoalkyl derivative of 3,3′,5,5′-tetraalkylbenzidine or a water-soluble salt thereof represented by the following general formula I:

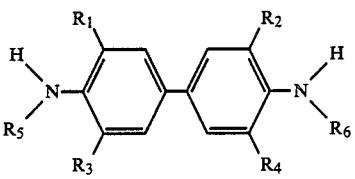

wherein $R_1$, $R_2$, $R_3$ and $R_4$ are straight-chain alkyl groups having 1 to 6 carbon atoms, selected from the group consisting of a methyl, ethyl, n-propyl, n-butyl, n-amyl and n-hexyl group, and one of $R_5$ and $R_6$ represents a sulfoalkyl group of the following formula II:

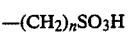

wherein n represents an integer of 1 to 6, the other one of $R_5$ and $R_6$ representing a member selected from the group consisting of a hydrogen atom and said sulfoalkyl group.

18. A process for assaying hydrogen peroxide, comprising the steps of:

preparing a test strip for assaying hydrogen peroxide comprising a composition for assaying hydrogen peroxide supported on an absorptive carrier applied to a support, wherein said composition comprises an enzyme, a buffer and a chromogen, said chromogen comprising a sulfoalkyl derivative of a 3,3′,5,5′-tetraalkylbenzidine or a water-soluble salt thereof represented by the following general formula I:

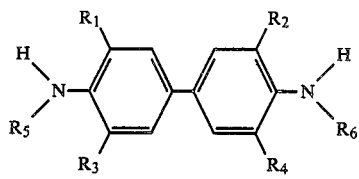 (I)

wherein $R_1$, $R_2$, $R_3$ and $R_4$ are straight-chain alkyl groups having 1 to 6 carbon atoms, selected from the group consisting of a methyl, ethyl, n-propyl, n-butyl, n-amyl and n-hexyl group, and one of $R_5$ and $R_6$ represents a sulfoalkyl group of the following formula II:

—$(CH_2)_nSO_3H$ (II)

wherein n represents an integer of 1 to 6, the other one of $R_5$ and $R_6$ representing a member selected from the group consisting of a hydrogen atom and said sulfoalkyl group.

* * * * *